United States Patent [19]

Rogier

[11] 4,229,376

[45] Oct. 21, 1980

[54] POLYCYCLIC POLYAMINES

[75] Inventor: Edgar R. Rogier, Minnetonka, Minn.

[73] Assignee: Henkel Corporation, Minneapolis, Minn.

[21] Appl. No.: 74,368

[22] Filed: Sep. 10, 1979

[51] Int. Cl.$^2$ .......................................... C07C 87/40
[52] U.S. Cl. ........................ 260/563 P; 260/18 EP; 260/563 D; 528/98; 528/122; 528/407
[58] Field of Search ................................... 260/563 P

[56] References Cited

U.S. PATENT DOCUMENTS

| | | | |
|---|---|---|---|
| 3,006,954 | 10/1961 | Ramey et al. | 260/563 P X |
| 3,231,595 | 1/1966 | Brotherton et al. | 260/563 P X |
| 3,238,251 | 3/1966 | Williams | 260/563 P X |
| 3,317,469 | 5/1967 | Feichtinger et al. | 260/563 R X |
| 3,386,924 | 6/1968 | Steden et al. | 260/563 P X |
| 3,409,659 | 11/1968 | Pruett et al. | 260/563 P X |
| 3,432,552 | 3/1969 | Kiefer et al. | 260/563 P |
| 3,470,248 | 9/1969 | Brotherton et al. | 260/563 P |
| 3,787,371 | 1/1974 | Brinkmann et al. | 528/324 |

FOREIGN PATENT DOCUMENTS

| | | | |
|---|---|---|---|
| 2641662 | 3/1978 | Fed. Rep. of Germany | 260/563 P |
| 51-80850 | 7/1976 | Japan | 260/563 P |
| 54-04992 | 12/1979 | Japan | 260/563 P |
| 1266016 | 3/1972 | United Kingdom | 260/563 P |

OTHER PUBLICATIONS

Badische Anilin, "Chem. Ab.", vol. 65, Ab. No. 15250$^a$ (1966).

*Primary Examiner*—John Doll
*Attorney, Agent, or Firm*—Forrest L. Collins

[57] ABSTRACT

Disclosed herein are tricyclic and pentacyclic polyamines having a secondary or tertiary amine group on an amine functional substituent and at least one primary amine group on each of two amine functional substituents in the molecule. These compounds function excellently as non-visably carbonating epoxy curing agents and in addition unlike most other amines exhibit a mild amine odor.

10 Claims, No Drawings

POLYCYCLIC POLYAMINES

BACKGROUND OF THE INVENTION

1. Field of the Invention

The present invention describes amine compounds suitable for use as epoxy curing agents and other utilities similar to that of conventional amines.

2. Description of the Art Practice

Tricyclic polyamines of various types are described in U.S. Pat. No. 3,470,248 issued Sept. 30, 1969 to Brotherton et al. The materials described in the Brotherton et al patent are stated to be useful in the resin art such as in the preparation of urethane polymers, polyamides and polyurethane polyurea elastomers. U.S. Pat. No. 3,787,371 issued Jan. 22, 1974 to Brinkmann et al discloses bis(aminomethyl)-tricyclo-decanes which are stated to be useful in the formation of clear polyamides.

U.S. Pat. No. 3,317,469 issued May 2, 1967 to Feichtinger et al discloses the use of materials denominated as di(aminomethyl)tricylcodecane for use as epoxy curing agents. It is also stated in Feichtinger et al that the diamines produced therein are clear, colorless, mobile liquids of weak odor. Wagner et al in German OLS 2641662 published Mar. 23, 1978 discloses tricyclodecane derivatives having amine functionality which may be condensed with adipic acid, acrylic acid, 2-hydroxyethylacrylate, or N-methylol acrylamide for use as storage stable radiation hardenable printing inks. British Pat. No. 1,266,016 published Mar. 8, 1972 and naming Wilhelm Becker as an inventor discloses the use of bis(aminomethyl) tricyclodecane as a curing agent for polyglycidyl ethers. In Japanese published patent application 54-4992 published Jan. 16, 1979 naming Kaya as inventor bisaminomethyl compounds possessing at least one bicyclo[2.2.1]-heptane ring as modified epoxy curing agents are reported. It is stated therein that the starting compounds having high reactivity thereby making control of the cure extremely difficult. It is also noted that the basic compounds disclosed therein exhibit a high degree of hygroscopicity and that the obtained epoxy paint film shows a whitish cloudiness, apparently from carbonation, at high humidity. Kaya states he cures the defect of high reactivity by partially adducting the amine with a material such as acrylonitrile. However, this solution is incomplete as the acrylonitrile may be split off during cure. In any event, the Kaya material reduces functionality thereby providing a much lower cross-link density which is disadvantageous.

Through the specification and claims percentages and ratios are given by weight and temperatures are in degrees of Celsius unless otherwise indicated. To the extent that each of the foregoing references are applicable to the present invention it is specifically herein incorporated by reference.

SUMMARY OF THE INVENTION

The present invention discloses polycyclic polyamines of the formula:

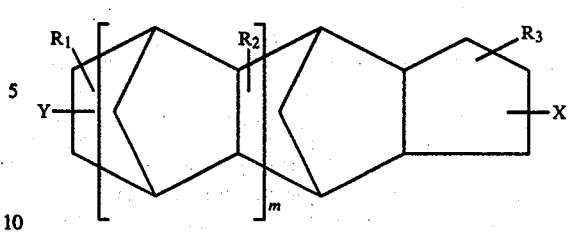

wherein the above formula m is equal to 0 or 1; x and y are selected from the group consisting of:
—$CH_2NH_2$; —$CH_2NH(CH_2CHR_4CH_2NH_2)$; and
—$CH_2N(CH_2CHR_4CH_2NH_2)_2$, and mixtures thereof,
wherein $R_1$, $R_2$, $R_3$, and $R_4$ are hydrogen or methyl and mixtures thereof, provided that both X and Y may not be $CH_2NH_2$.

The present invention also describes the above compound cured with an epoxy resin having an epoxide functionality.

DETAILED DESCRIPTION OF THE INVENTION

The present invention relates to the formation and utilization of polycyclic polyamines which are particularly useful as epoxy curing agents. The starting material for preparing the polycyclic polyamines of the present invention are known by their trivial names of dicyclopentadiene and tricyclopentadiene. Both materials are polymers of cyclopentadiene (or its methylated derivative) which following polymerization are hydroformylated to give the corresponding dialdehyde which is then subjected to a reductive amination to give the corresponding bis(aminomethyl) structure such as is shown in the Brinkmann et al patent.

The bis(aminomethyl) compounds which are substantially free from any odor are then reacted with an acrylonitrile component selected from the group consisting of acrylonitrile or methyacrylonitrile. The acrylonitrile component adds to each primary amine functional group of the starting diamine in 1:1 or 2:1 mole ratio respectively. The definition of the amine functional substituent is that amine group of the starting diamine represented by X and Y independently in the above structural formulas.

Thus the addition of the acrylonitrile component may be varied depending on the number of desired amine functionality required for a particular use. For instance, the addition of two moles of the acrylonitrile component to the starting diamine will give substantial amounts of a disecondary amine which when upon reduction will become a disecondary diprimary amine. When adding sufficient amounts of acrylonitrile component to replace each of the primary amine hydrogens on the starting diamine it is possible after hydrogenation to obtain a compound which is a ditertiary, tetraprimary amine. Of course, also found in mixture with the aforementioned particularly desirable components will be the incomplete acrylonitrile addition products giving rise to values of X or Y wherein the corresponding monotertiary, monosecondary, triprimary amine is obtained after hydrogenation. A particularly interesting product which can be made is the monosecondary diprimary amine corresponding to only having either X or Y converted to the diprimary amine structure by addition and reduction of the acrylonitrile component.

The principal compounds with which the present invention is concerned are described below with reference to the substituents shown in the Summary of the Invention. The ring number system for the tricyclodecane ring system is shown in figure (II). The later formulas, while omitting the methyl groups $R_1$ and $R_2$, are also included in the preferred derivatives as are mixed systems where $R_1$ or $R_2$ is methyl and the other substituent is hydrogen. Similarly, the compounds in II through VIII in which $R_4$ represents the methyl from the use of methacrylonitrile and its mixtures with acrylonitrile are included.

The compounds shown by III are a mixture of isomeric triamines having the chemical name 3(4)(5)-[N-(3-aminopropyl)aminomethyl]-8-aminomethyl tricyclo $(5,2,1,0^{2,6})$ decane while the reverse triamines shown as IV are named 3(4)(5)-Aminomethyl-8-[N-(3-aminopropyl) aminomethyl] tricyclo $(5,2,1,0^{2,6})$decane. The compounds shown in V are 3(4)(5), 8-bis[N-(3-aminopropyl)aminomethyl] tricyclo $(5,2,1,0^{2,6})$ decane. The pentamines shown in figure (VI) are named 3(4)(5)-N,N-bis(3-aminopropyl) aminomethyl, 8-N(3-aminopropyl) aminomethyl tricyclo $(5,2,1,0^{2,6})$ decane while the reverse pentamines (VII) are 3(4)(5)-N-(3-aminopropyl)aminomethyl, 8-N,N-bis(3-aminopropyl)-aminomethyl tricyclo $(5,2,1,0^{2,6})$ decane. The hexamine compounds shown in (VIII) are appropriately named as 3(4)(5), 8-bis[N,N-bis(3-aminopropyl)aminomethyl] tricyclo $(5,2,1,0^{2,6})$ decane.

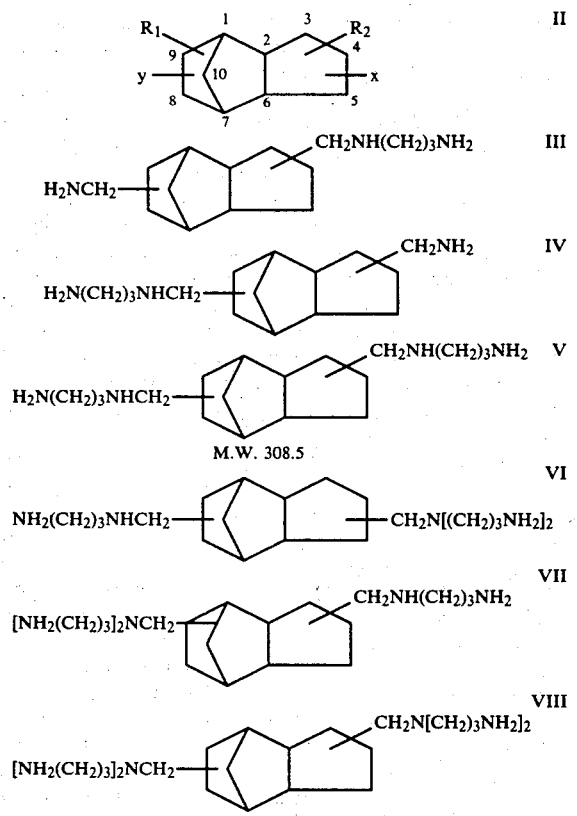

A facet that has been noted as a particular advantage of the present invention over the acrylonitrile modified polycyclic amines of the Kaya patent is that the present products are substantially free from any acrylonitrile following hydrogenation and thus acrylonitrile cannot be liberated during the cure of the resin with an epoxy compound. It should also be observed that a distinct advantage is found in the materials of the present invention in that they are excellent polyfunctional epoxy curing agents leading to substantially crosslinked materials. The present compounds are also extremely beneficial in that they do not visibly carbonate or form solid insoluble carbonates upon storage or use. Thus while the compounds of the present invention may carbonate, the whitish precipitate as described in the Kaya patent does not occur and thus clear epoxy compounds are obtained. The present products are also found to carbonate less upon curing than diethylenetriamine (DETA), a widely used amine.

In the present invention it is most preferred in the description of manufacture of the polycyclic polyamines herein that $R_1$, $R_2$ and $R_3$ are each hydrogen on the starting polycyclic polyamine. It is also preferred that the value of $R_4$ be hydrogen corresponding to the use of acrylonitrile as the original starting material. This is particularly important when forming higher polyamines to avoid the steric hinderance caused by the use of methacrylonitrile. However, if methacrylonitrile is employed several suitable advantages are still observed for that compound.

The value of m given as 0 corresponds to the tricyclo compound; where m is 1 the corresponding pentacyclo compound is obtained. As previously noted, x and y may be identical or divergent. That is, the preferred compounds have m equal to 0 and have 3 or 4 amine groups although the corresponding pentamines and hexamines are highly useful. In practice, the higher polycyclic polyamines of the invention may be mixed with the starting bisaminomethyl compound and may thus be utilized in mixtures preferably of from about 90:10 to 50:50 respectively.

As previously noted, it is highly desirable that all of the nitrile groups be reduced by hydrogenation. This is done to avoid liberation of acrylonitrile upon cure with the epoxy compound. It was observed by Kaya that the presence of unreduced nitrile on the starting material slows the reactivity of the resin with the possibility that the coating is adversely affected.

It should also be noted that in addition to the primary utility of the present compounds as epoxy curing agents that they may be adducted with materials such as caprolactam or polyfunctional acids to form polyamides such as through the use of adipic acid or the phthalic acids. In general, the compounds of the present invention may be utilized for any of the conventional uses of polyamines. It is also noted that the compounds of the present invention are not particularly hygroscopic.

A further distinct advantage of the compounds of the present invention over the starting amine is that of the mild but definite amine odor in the compounds of the present invention. The starting amino-methyl compounds do not have any pronounced amine odor and thus their use by employees in the coating industry must be closely monitored to avoid any adverse affects to the employees. Whereas the present amines due to their amine odor are self-warning as to their concentration in a coatings plant.

The following is a description of the manufacture of the polycyclic polyamines claimed in the present invention.

Conveniently the starting polycyclic amine, a solvent and the nitrile are placed in an enclosed vessel and stirred and heated under reflux for a period of from about 1 to 3 hours at which time the reaction is complete. Inasmuch as the reaction is exothermic, little energy need be applied. However, the temperature of the reaction vessel should be maintained between about 30 and 90 degrees C. to ensure substantial completion of the reaction. The reaction mixture is thereafter hydrogenated preferably using a hydrogenation catalyst such as Raney nickel, Raney cobalt, or platinum to form the polycyclic polyamine (I). Where the nitrile is not completely consumed in the addition reaction it is desirable to flush the excess out of the vessel prior to the hydrogenation to avoid undesirable byproducts.

The formation of the polycyclic polyamine (I) is accomplished by hydrogenating the corresponding nitrilodiamine. The conditions for the hydrogenation are as previously noted preferably using a hydrogenation catalyst. Again, any excess nitrile should be removed prior to hydrogenation. The pressure for the hydrogenation in absolute units should not be less than 10 atmospheres and should be conducted at a temperature from about 60 degrees C. to about 160 degrees C. Preferably the hydrogenation conditions are such that the pressure is at least about 50 atmospheres absolute and from about 80 degrees C. to about 140 degrees C. It is preferred that during the hydrogenation reaction that ammonia be added to the reaction vessel to minimize the tendency of the reactants to condense with itself and liberate ammonia gas. The total pressure requirements for the mixture of the reactants, the hydrogen gas and the ammonia are generally required to be in the range of about 50 to about 100 atmospheres or higher.

The polycyclic polyamines so formed are then reacted with any conventional epoxy resin to form the curable coating compositions of the present invention. These epoxy resins may be both solid or liquid materials. It is, of course, preferable that the epoxy resin be a liquid material to facilitate mixing and enhance pot life.

In general, the most commonly available epoxy resins are those which are the reaction products of epichlorohydrin and bis(parahydroxyphenyl) propane, "bisphenol A," such as are described in a U.S. Pat. No. McCaleb et al (3,280,074) incorporated herein be reference. Alternatively, "bisphenol F" which is bis(parahydroxyphenyl)methane may be utilized.

Other such epoxy resins are those which are the reaction product of epichlorohydrin and bis(parahydroxyphenyl) sulfone. Still another group of epoxy compounds which may be employed are the glycidyl esters of the polymeric fat acids. These glycidyl esters are obtained by reacting the polymeric fat acids with polyfunctional halohydrins such as epichlorohydrins. In addition, the glycidyl esters are also commercially available epoxide materials. The glycidyl esters of the polymeric fat acids are also useful in the present invention and are also described in the McCaleb et al patent.

The polymeric fat acids are well known materials, commercially available, which are the products from the polymerization of unsaturated fatty acids to provide a mixture of dibasic and higher polymeric fat acids. The polymeric fat acids are those resulting from the polymerization of the drying or semi-drying oils or the free acids or the simple aliphatic alcohol esters of such acids. Suitable drying or semi-drying oils include soybean, linseed, tung, perilla, oiticia, cottonseed, corn, sunflower, safflower, dehydrated castor oil and the like. The term "polymeric fat acids" as used herein and as understood in the art, is intended to include the polymerized mixture of acids which usually contain a predominant portion of dimer acids, a small quantity of trimer and higher polymeric fat acids and some residual monomers.

In general, the most readily available naturally occurring polyunsaturated acid available in large quantities is linoleic acid. Accordingly, it should be appreciated that polymeric fat acids will, as a practical matter, result from fatty acid mixtures that contain a preponderance of linoleic acid and will thus generally be composed largely of dimerized linoleic acid. However, polymerized fatty acids may be prepared from the naturally occurring fatty acids having from 8 to 22, and preferably 16 to 20, carbon atoms. Illustrative thereof are oleic, linolenic, palmitoleic, and the like.

Other types of epoxy resins which may be cured with the present products and which are commercially available epoxy materials are the polyglycidyl ethers of tetraphenols which have two hydroxy aryl groups at each end of an aliphatic hydrocarbon chain. These polyglycidyl ethers are obtained by reacting the tetraphenols with polyfunctional halohydrins such as epichlorohydrin. The tetraphenols used in preparing the polyglycidyl ethers are a known class of compounds readily obtained by condensing the appropriate dialdehyde with the desired phenol. Typical tetraphenols useful in the preparation of these epoxy resins are the alpha, omega, omega-tetrakis (hydroxyphenol) alkanes, such as 1,1,2,2-tetrakis(hydroxyphenol)ethane, 1,1,4,4-tetrakis(hydroxyphenol)butane, 1,1,4,4-tetrakis(hydroxyphenol)2-ethylbutane and the like. The epoxy resin reaction product of the epichlorohydrin and tetraphenol is also shown in the McCaleb et al patent with the appropriate limitations shown therein. A preferred group of aliphatic polyglycidyl ethers are those described in the pending application of Rogier which are prepared from hydroxymethyl alchols. Other glycidyl ethers of aliphatic polyols may be employed.

Still another group of epoxide materials are the epoxidized novolac resins. Such resins are well-known substances and readily available commercially as evidenced in McCaleb et al.

In general, these resins are obtained by epoxidation of the well-known novolac resins. The novolac resins, as is known in the art, are produced by condensing the phenol with an aldehyde in the presence of an acid catalyst. Although novolac resins from formaldehyde are generally employed, novolac resins from other aldehydes such as, for example, acetaldehyde, chloral, butyraldehyde, furfural, and the like, may also be used. The alkyl groups, if present, may have a straight or a branched chain. Illustrative of the alkylphenol from which the novolac resins may be derived are cresol, butylphenol, tertiary butylphenol, tertiary amylphenol, hexylphenol, 2-ethylhexylphenol, nonylphenol, decylphenol, dodecylphenol, and the like. It is generally preferred, but not essential, that the alkyl substituent be in the para position in the phenolic nucleus. However, novolac resins in which the alkyl groups are in the ortho position have been prepared.

The epoxidized novolac resin is formed in the well-known manner by adding the novolac resin to the epichlorohydrin and then adding an alkali metal hydroxide to the mixture so as to effect the desired condensation reaction.

In addition, other epoxy resins which may be cured with the curing agent of the present invention are the glycidyl ethers of the polyalkylene glycols, epoxidized olefins such as epoxidized polybutadiene and epoxidized cyclohexanes.

In general, the epoxy resins may be described as those having terminal 1,2-epoxide groups.

In addition, the epoxy resins may be characterized further by reference to their epoxy equivalent weight, the epoxy equivalent weight of pure epoxy resin being the mean molecular weight of the resins divided by the mean number of epoxy radicals per molecule, or, in any case, the number of grams of epoxy resin equivalent to one epoxy group or one gram equivalent of epoxide. The epoxy resinous materials employed in this invention have an epoxy equivalent weight of from about 140 to about 2,000, preferably from about 140 to 300.

Liquid modifiers such as triphenyl phosphite (Mod-Epox), a tertiary amine (DMP30), nonyl phenol, and flow control agents such as silicone resins and oils may be used to achieve quicker curing or smoother films when dried under adverse conditions. Liquid plasticizers such as dibutyl phthalate may be added. The addition of judicious amounts of triphenyl phosphite or fluid plasticizers would reduce viscosity further to facilitate handling. Small amounts of solvents may be used to secure even lower viscosity, but of course, the combination would not then be solvent free.

Solid modifiers may be used such as pigments and fillers normally used in paints, or sand which might be added to produce trowelling concrete toppings or floor coatings. Treated clays and amorphous silica may be used to secure non-sagging thick coatings for vertical surfaces.

The following are examples of the present invention:

EXAMPLE I

3(4)(5), 8-diformyltricyclo $(5,2,1,0^{2,6})$ decane is prepared as the initial starting material from dicyclopentadiene DCPD.

The process is conducted by utilizing a 1 liter, 316 SS Magnadrive autoclave equipped with a turbine stirrer, heat exchange coils and a thermocouple. This apparatus is charged with 203 g (1.54 moles) of the DCPD. 244 g of toluene, 2.0 g of 5% rhodium on alumina and 0.88 g of triphenylphosphite are added. The latter materials are utilized as the catalyst. The autoclave is then purged with nitrogen and pressurized with carbon monoxide-hydrogen (1:1) mole ratio to 70 atmospheres of pressure. The reaction mixture is then stirred and steam heated to 70 degrees C. and following a period of about 13 minutes gas uptake is observed.

The temperature in the reaction vessel is slowly increased to 101 degrees C. over a period of about 40 minutes where gas uptake was noted to have essentially stopped.

A gas chromatography analysis of the sample taken at this time indicates a 97% conversion to 3(4)(5), 8-formyltricyclodecane. The temperature was increased to 120–123 degrees C. and held at this temperature for 1.8 hours at 70 atmospheres. The autoclave is then cooled to 50 degrees C., vented, purged with nitrogen and discharged through a pressure filter. Vacuum distillation of toluene from the reaction mixture yielded 278 g of the 3(4)(5), 8-diformyltricyclo $(5,2,1,0^{2,6})$ decane. The product is observed by GLC, IR and NMR to consist primarily of two diformyl isomers of the tricyclodecane.

EXAMPLE II

The product of Example I is converted to 3(4)(5)8-bis(aminomethyl) tricyclo $(5,2,1,0^{2,6})$ decane.

An autoclave, such as the one used in Example I, is charged with 78.5 g of wet Raney nickel (washed with ethanol), 350 g of ethanol and 312 g of ammonia. The autoclave is heated to 128 degrees C., and the resulting pressure is observed as approximately 48 atmospheres.

The autoclave is then pressurized to about 62 atmospheres with hydrogen and the addition of 679 g of the product of Example I dissolved in 496 g of ethanol is started using a positive displacement pump.

The temperature during the addition is controlled between 125–132 degrees C. and the pressure is at from about 55 to 63 atmospheres by the hydrogen addition.

The addition of the product of Example I is completed in about 41 minutes. This reaction mixture is then held under these conditions for an additional 2.3 hours and cooled to 55 degrees C., vented, purged with nitrogen and discharged through a pressure filter. The filtrate is then stripped under reduced pressure (60 degrees C. at less than 1 torr) to yield 680 g of 3(4)(5),8-bis(aminomethyl)tricyclo $(5,2,1,0^{2,6})$ decane having an amine eq. wt. = 99.8.

EXAMPLE III

The product of Example II is converted to the corresponding 3(4)(5),8-bis[N(2-cyanoethyl)-aminomethyl] tricyclo $(5,2,1,0^{2,6})$ decane.

This transformation is accomplished utilizing a 2 liter glass reaction flask equipped with stirrer, heat exchange coil, and thermocouple. Into this reaction flask is introduced 667 g (3.44 moles) of the product of Example II under a blanket of nitrogen. The system is heated to 40 degrees C. and 391 g (7.37 moles) of acrylonitrile is metered into the reaction system over a period of one hour with stirring.

The temperature of this reaction mixture is then maintained at 40 degrees C. for an additional hour and then increased to 60 degrees C. for 5.5 hours. The product is then stripped under vacuum (less than 1 torr) for one hour. Total yield of product of Example III is 1018 g.

EXAMPLE IV

The dinitrile product obtained in Example III is converted through hydrogenation to the desired products of the present invention as follows.

Into a 1 liter, 316 SS Magnadrive autoclave is charged 325 g (1.08 moles) of the dinitrile of Example III. 168 g of ethanol and 37.6 g of ethanol wet Raney nickel are also added. The autoclave is sealed, flushed with nitrogen and charged with 41 g of liquid ammonia.

The system is then charged with hydrogen to 99 atmospheres pressure and heating and stirring is started. The temperature then increases to 134 degrees C. over a period of 1.8 hours and is maintained at 132–134 degrees C. at about 91 atmospheres for 1.67 hours.

The autoclave is then cooled to 43 degrees C., vented to ambient pressure, flushed with nitrogen and the contents discharged through a pressure filter. The filtrate is stripped of volatiles in a rotary evaporator at 65 degrees C. and a vacuum of less than 1 torr. The yield of crude amine is observed as follows: 2.9% of dicyclopentadiene (starting material), the triamine, is shown as compounds III and IV are present at 33.6% and the tetramine shown as Product V is present at 63.3%.

The products may be separated from one another by first running the crude amine through a wiped-film distillation apparatus and then by separating the various components by using a fractional distillation using a 15 plate, 50 mm O.D. Oldershaw fractionating column.

The above example may be varied by reacting the diamine of Example II with sufficient amounts of acrylonitrile followed by the present hydrogenation process to obtain compounds VI, VII, and VIII. These materials may also be separated from one another through the foregoing process to yield essentially pure materials.

What is claimed is:

1. A polyamine of the formula:

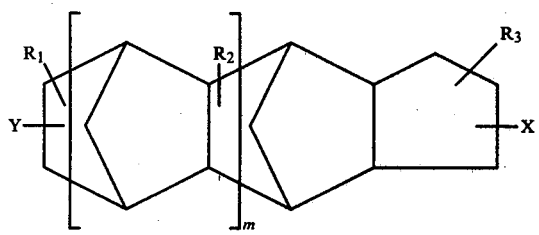

wherein the above formula m is equal to 0 or 1; x and y are selected from the group consisting of:

—$CH_2NH_2$; —$CH_2NH(CH_2CHR_4CH_2NH_2)$; and
—$CH_2N(CH_2CHR_4CH_2NH_2)_2$, and mixtures thereof, wherein $R_1$, $R_2$, $R_3$, and $R_4$ are hydrogen or methyl and mixtures thereof, provided that both x and y may not be $CH_2NH_2$.

2. The compositions of claim 1 wherein m is equal to 0.

3. The composition of claim 1 wherein $R_1$, $R_2$ and $R_3$ are each hydrogen.

4. The composition of claim 1 wherein $R_4$ is hydrogen.

5. 3(4)(5)-[N-(3-aminopropyl)aminomethyl]-8-aminomethyltricyclo $(5,2,1,0^{2,6})$ decane.

6. 3(4)(5)-aminomethyl-8-[N-(3-aminopropyl) aminomethyl] tricyclo $(5,2,1,0^{2,6})$ decane.

7. 3(4)(5), 8-bis[N-(3-aminopropyl)aminomethyl] tricyclo $(5,2,1,0^{2,6})$ decane.

8. 3(4)(5)-N,N-bis(3-aminopropyl) aminomethyl, 8-N(3-aminopropyl) aminomethyl tricyclo $(5,2,1,0^{2,6})$ decane.

9. 3(4)(5)-N(3-aminopropyl)aminomethyl, 8-N,N-bis(3-aminopropyl)aminomethyl tricyclo $(5,2,1,0^{2,6})$ decane.

10. 3(4)(5), 8-bis[N,N-bis(3aminopropyl)aminomethyl] tricyclo $(5,2,1,0^{2,6})$ decane.

* * * * *